(12) United States Patent
Qiu

(10) Patent No.: US 7,915,382 B2
(45) Date of Patent: Mar. 29, 2011

(54) ANTIFUNGAL BIFUNCTIONAL MOLECULES, METHODS OF CONSTRUCTION AND METHODS OF TREATING FUNGAL INFECTION THEREWITH

(75) Inventor: Xiao-Qing Qiu, Chengdu (CN)

(73) Assignee: Phermonicin Biotech, Ltd., Tortola (VG)

( * ) Notice: Subject to any disclaimer, the term of this patent is extended or adjusted under 35 U.S.C. 154(b) by 695 days.

(21) Appl. No.: 11/338,117

(22) Filed: Jan. 23, 2006

(65) Prior Publication Data

US 2006/0264370 A1 Nov. 23, 2006

(30) Foreign Application Priority Data

Jan. 21, 2005 (CN) .......................... 2005 1 0020219

(51) Int. Cl.
*C07K 1/00* (2006.01)

(52) U.S. Cl. ........ 530/350; 530/300; 435/252; 435/325; 435/7.1

(58) Field of Classification Search ........................ None
See application file for complete search history.

(56) References Cited

U.S. PATENT DOCUMENTS

2003/0078207 A1 * 4/2003 Qiu .................................. 514/12
2003/0113293 A1 * 6/2003 Bermudes et al. ........... 424/93.2

OTHER PUBLICATIONS

Mankovich et al. (Bacteriology, vol. 168, pp. 228-236, 1986).*

* cited by examiner

*Primary Examiner* — Hope A Robinson
(74) *Attorney, Agent, or Firm* — Blakely, Sokoloff, Taylor & Zafman LLP.

(57) ABSTRACT

The present invention is directed to fusion peptides comprising a fungal targeting agent and a channel-forming domain consisting essentially of amino acids 451-626 of colicin Ia, as well as the polynucleotides encoding the peptides of the invention. The fusion peptides of the peptides of the present invention are particularly useful for the treatment of fungal infections in a wide variety of organisms.

4 Claims, 9 Drawing Sheets

SEQUENCE LISTING

<160> NUMBER OF SEQ ID NOS: 8

<210> SEQ ID NO 1
<211> LENGTH: 528
<212> TYPE: DNA
<213> ORGANISM: Escherichia coli
<220> FEATURE:
<221> NAME/KEY: misc_feature
<222> LOCATION: (1)..(528)
<223> OTHER INFORMATION: Gene of colicin Ia

<400> SEQUENCE: 1

```
gacgcaatta atttcacaac agagttcctg aaatcagttt cagaaaaata tggtgcaaaa        60
gctgagcagt tagccagaga gatggccggg caggctaaag ggaagaaaat acgtaatgtt       120
gaagaggcat taaaaacgta tgaaaagtac cgggctgaca ttaacaaaaa aattaatgca       180
aaagatcgtg cagcgattgc cgcagcccct gagtctgtga agctgtctga tatatcgtct       240
aatctgaaca gattcagtcg gggactggga tatgcaggaa aatttacaag tcttgctgac       300
tggatcactg agtttggtaa ggctgtccgg acagagaact ggcgtcctct ttttgttaaa       360
acagaaacca tcatagcagg caatgccgca acggctcttg tggcactggt cttcagtatt       420
cttaccggaa gcgctttagg cattatcggg tatggtttac tgatggctgt caccggtgcg       480
ctgattgatg aatcgcttgt ggaaaaagcg aataagttct ggggtatt                   528
```

```
<210> SEQ ID NO 2
<211> LENGTH: 42
<212> TYPE: DNA
<213> ORGANISM: Artificial Sequence
<220> FEATURE:
<223> OTHER INFORMATION: Oligonucleotide encoding Candida albicans
      a-mating pheromone

<400> SEQUENCE: 2
gggtttcgtc tcacaaactt cggatacttt gagcccggca aa                    42

<210> SEQ ID NO 3
<211> LENGTH: 14
<212> TYPE: PRT
<213> ORGANISM: Artificial Sequence
<220> FEATURE:
<223> OTHER INFORMATION: Amino acid sequence of Candida albicans
      a-mating pheromone

<400> SEQUENCE: 3

Gly Phe Arg Leu Tyr Asn Phe Gly Tyr Phe Glu Pro Gly Lys
1               5                   10

<210> SEQ ID NO 4
<211> LENGTH: 570
<212> TYPE: DNA
<213> ORGANISM: Artificial Sequence
<220> FEATURE:
<223> OTHER INFORMATION: Gene encoding Ph-CA1

<400> SEQUENCE: 4
gacgcaatta atttcacaac agagttcctg aaatcagttt cagaaaaata tggtgcaaaa    60
gctgagcagt tagccagaga gatggccggg caggctaaag gaagaaaat acgtaatgtt    120 gaagaggcat taaaaacgta tgaaaagtac cgggctgaca ttaacaaaaa aattaatgca    180
aaagatcgtg cagcgattgc cgcagccctt gagtctgtga agctgtctga tatatcgtct    240
aatctgaaca gattcagtcg gggactggga tatgcaggaa aatttacaag tcttgctgac    300
tggatcactg agtttggtaa ggctgtccgg acagagaact ggcgtcctct ttttgttaaa    360
acagaaacca tcatagcagg caatgccgca acggctcttg tggcactggt cttcagtatt    420
cttaccggaa gcgctttagg cattatcggg tatggtttac tgatggctgt caccggtgcg    480
ctgattgatg aatcgcttgt ggaaaaagcg aataagttct ggggtattgg gtttcgtctc    540
acaaacttcg gatactttga gcccggcaaa                                    570

<210> SEQ ID NO 5
<211> LENGTH: 190
<212> TYPE: PRT
<213> ORGANISM: Artificial Sequence
<220> FEATURE:
<223> OTHER INFORMATION: Amino acid sequence of Ph-CA1

<400> SEQUENCE: 5

Asp Ala Ile Asn Phe Thr Thr Glu Phe Leu Lys Ser Val Ser Glu Lys
1               5                   10                  15

Tyr Gly Ala Lys Ala Glu Gln Leu Ala Arg Glu Met Ala Gly Gln Ala
            20                  25                  30

Lys Gly Lys Lys Ile Arg Asn Val Glu Glu Ala Leu Lys Thr Tyr Glu
        35                  40                  45

Lys Tyr Arg Ala Asp Ile Asn Lys Lys Ile Asn Ala Lys Asp Arg Ala
    50                  55                  60

Ala Ile Ala Ala Ala Leu Glu Ser Val Lys Leu Ser Asp Ile Ser Ser
65                  70                  75                  80
```

```
Asn Leu Asn Arg Phe Ser Arg Gly Leu Gly Tyr Ala Gly Lys Phe Thr
                85                  90                  95

Ser Leu Ala Asp Trp Ile Thr Glu Phe Gly Lys Ala Val Arg Thr Glu
            100                 105                 110

Asn Trp Arg Pro Leu Phe Val Lys Thr Glu Thr Ile Ile Ala Gly Asn
        115                 120                 125

Ala Ala Thr Ala Leu Val Ala Leu Val Phe Ser Ile Leu Thr Gly Ser
130                 135                 140

Ala Leu Gly Ile Ile Gly Tyr Gly Leu Leu Met Ala Val Thr Gly Ala
145                 150                 155                 160

Leu Ile Asp Glu Ser Leu Val Glu Lys Ala Asn Lys Phe Trp Gly Ile
                165                 170                 175

Gly Phe Arg Leu Tyr Asn Phe Gly Tyr Phe Glu Pro Gly Lys
            180                 185                 190
```

<210> SEQ ID NO 6
<211> LENGTH: 570
<212> TYPE: DNA
<213> ORGANISM: Artificial Sequence
<220> FEATURE:
<223> OTHER INFORMATION: Gene encoding Ph-CA2

<400> SEQUENCE: 6

```
gggtttcgtc tcacaaactt cggatacttt gagcccggca agacgcaat  taatttcaca    60
acagagttcc tgaaatcagt ttcagaaaaa tatggtgcaa aagctgagca gttagccaga   120
gagatggccg ggcaggctaa agggaagaaa atacgtaatg ttgaagaggc attaaaaacg   180
tatgaaaagt accgggctga cattaacaaa aaaattaatg caaaagatcg tgcagcgatt   240
gccgcagccc ttgagtctgt gaagctgtct gatatatcgt ctaatctgaa cagattcagt   300
cggggactgg gatatgcagg aaaatttaca agtcttgctg actggatcac tgagtttggt   360
aaggctgtcc ggacagagaa ctggcgtcct cttttttgtta aaacagaaac catcatagca   420
ggcaatgccg caacggctct tgtggcactg tcttcagta ttcttaccgg aagcgcttta   480
ggcattatcg gtatggtttt actgatggct gtcaccggtg cgctgattga tgaatcgctt   540
gtggaaaaag cgaataagtt ctggggtatt                                    570
```

<210> SEQ ID NO 7
<211> LENGTH: 190
<212> TYPE: PRT
<213> ORGANISM: Artificial Sequence
<220> FEATURE:
<223> OTHER INFORMATION: Amino acid sequence of Ph-CA2

<400> SEQUENCE: 7

```
Gly Phe Arg Leu Tyr Asn Phe Gly Tyr Phe Glu Pro Gly Lys Asp Ala
1               5                   10                  15

Ile Asn Phe Thr Thr Glu Phe Leu Lys Ser Val Ser Glu Lys Tyr Gly
            20                  25                  30

Ala Lys Ala Glu Gln Leu Ala Arg Glu Met Ala Gly Gln Ala Lys Gly
        35                  40                  45

Lys Lys Ile Arg Asn Val Glu Glu Ala Leu Lys Thr Tyr Glu Lys Tyr
    50                  55                  60

Arg Ala Asp Ile Asn Lys Lys Ile Asn Ala Lys Asp Arg Ala Ala Ile
65                  70                  75                  80

Ala Ala Ala Leu Glu Ser Val Lys Leu Ser Asp Ile Ser Ser Asn Leu
                85                  90                  95
```

-continued

```
Asn Arg Phe Ser Arg Gly Leu Gly Tyr Ala Gly Lys Phe Thr Ser Leu
            100                 105                 110

Ala Asp Trp Ile Thr Glu Phe Gly Lys Ala Val Arg Thr Glu Asn Trp
            115                 120                 125

Arg Pro Leu Phe Val Lys Thr Glu Thr Ile Ile Ala Gly Asn Ala Ala
            130                 135                 140

Thr Ala Leu Val Ala Leu Val Phe Ser Ile Leu Thr Gly Ser Ala Leu
145                 150                 155                 160

Gly Ile Ile Gly Tyr Gly Leu Leu Met Ala Val Thr Gly Ala Leu Ile
            165                 170                 175

Asp Glu Ser Leu Val Glu Lys Ala Asn Lys Phe Trp Gly Ile
            180                 185                 190

<210> SEQ ID NO 8
<211> LENGTH: 176
<212> TYPE: PRT
<213> ORGANISM: Escherichia coli

<400> SEQUENCE: 8

Asp Ala Ile Asn Phe Thr Thr Glu Phe Leu Lys Ser Val Ser Glu Lys
1               5                   10                  15

Tyr Gly Ala Lys Ala Glu Gln Leu Ala Arg Glu Met Ala Gly Gln Ala
            20                  25                  30

Lys Gly Lys Lys Ile Arg Asn Val Glu Glu Ala Leu Lys Thr Tyr Glu
            35                  40                  45

Lys Tyr Arg Ala Asp Ile Asn Lys Lys Ile Asn Ala Lys Asp Arg Ala
            50                  55                  60

Ala Ile Ala Ala Ala Leu Glu Ser Val Lys Leu Ser Asp Ile Ser Ser
65                  70                  75                  80

Asn Leu Asn Arg Phe Ser Arg Gly Leu Gly Tyr Ala Gly Lys Phe Thr
            85                  90                  95

Ser Leu Ala Asp Trp Ile Thr Glu Phe Gly Lys Ala Val Arg Thr Glu
            100                 105                 110

Asn Trp Arg Pro Leu Phe Val Lys Thr Glu Thr Ile Ile Ala Gly Asn
            115                 120                 125

Ala Ala Thr Ala Leu Val Ala Leu Val Phe Ser Ile Leu Thr Gly Ser
            130                 135                 140

Ala Leu Gly Ile Ile Gly Tyr Gly Leu Leu Met Ala Val Thr Gly Ala
145                 150                 155                 160

Leu Ile Asp Glu Ser Leu Val Glu Lys Ala Asn Lys Phe Trp Gly Ile
            165                 170                 175
```

ANTIFUNGAL BIFUNCTIONAL MOLECULES, METHODS OF CONSTRUCTION AND METHODS OF TREATING FUNGAL INFECTION THEREWITH

CROSS REFERENCE TO RELATED APPLICATIONS

This application claims priority under 35 U.S.C. §119(a) to Chinese Patent Application No. 2005100202199, filed on Jan. 21, 2005.

BACKGROUND OF THE INVENTION

1. Field of the Invention

The present invention is directed to novel peptide compounds, and methods of making and using the peptides for the treatment of fungal infections, e.g., *Candida albicans, Cryptococcus neoformans, Aspergillus flavus, Magnaporthe grisea* and *Fusarium moniforme*.

2. Related Art

Fungus is opportunistic pathogens in humans. Fungus typically does not infect healthy tissues, yet once tissue defense mechanisms have been compromised, they can readily infect the tissue. One typical model of this opportunistic fungal infection is candidiasis, which is caused by *Candida albicans*.

*Candida albicans* occurs as normal flora in the oral cavity, genitalia, large intestine, and skin of approximately 20% of humans. The risk of infection increases in children and pregnant women; people who use certain antibiotics or have nutritional and organic disease or immunodeficiency (e.g., AIDS) or trauma; and people with invasive devices, e.g., pacemakers. *Candida albicans* and its close relatives account for nearly 80% of nosocomial fungal infections and 30% of deaths from nosocomial infections in general.

Historically, opportunistic fungal infections in hospitalized patients were rather unusual. Textbooks from the past described these agents as common contaminants with weak pathogenic potential, and infections were considered extreme deviation form the normal. Older ideas concerning these so-called harmless contaminants are now challenged because in those days immunodeficient and debilitated patients had died from their afflictions long before fungal infection took place. However, currently, with the advent of innovative surgeries, drugs, and other therapies that maintain such patients for expected periods, the survival rates of patients have significantly increased and the number of compromised patients has thus increased. One clinical dilemma that cannot be completely eliminated, even with rigorous disinfections, is the exposure of such patients to potential fungal pathogens from even normal flora. Fungal infections in such high-risk patients progress rapidly and are difficult to diagnose and treat. In one study, fungi caused approximately 40% of the deaths from clinically acquired infections. Up to 5% of all nosocomial opportunistic fungi cause infections.

Fungi also present special problems in chemotherapy. A majority of chemotherapeutic drugs used in treating bacterial infection are generally ineffective in combating fungal infection. Moreover, the similarity between fungal and human cells often means drug toxic to fungal cells are capable of harming human cells. A few drugs with special antifungal properties have been developed for treatment of systemic and superficial fungal infections. For example, macrolide polyenes represented by amphotericin B, have a structure that mimics some cell membrane lipids. Amphotericin B which is isolated from a species of streptomycin is by far the most versatile and effective of all antifungal drugs. The azoles are broad-spectrum antifungal drugs with a complex ringed structure. As one of the most effective azole drugs, fluconazole, is used in patients with AIDS-related mycoses.

*Magnaporthe grisea* is the pathogen of a devastating fungal disease of rice plants known as rice blast. The fungus can also cause a similar disease in over 50 grasses, including economically important crops such as barley, wheat, and millet. *Fusarium* is another important genus of fungal pathogens, responsible for devastating diseases such as cereal scab.

SUMMARY OF THE INVENTION

The present invention is directed to novel peptides comprising a fungi specific targeting agent, e.g., a pathogenic fungal peptide pheromone, and channel-forming colicin or a channel-forming fragment thereof (also referred to herein as "domain"). Peptides comprising a pheromone as the fungi specific targeting agent, and a colicin domain, are referred to herein as "pheromonicin peptides".

The molecular structure of the formed peptides may have the C-terminus of colicin or a channel-forming domain linked with the N-terminus of a fungi specific targeting agent, e.g., a fungal pheromone, or the N-terminus of colicin may be linked with the C-terminus of a fungi specific targeting agent e.g., a fungal pheromone. The fungal pheromone can be from a pathogenic fungus, e.g., *Candidas*. The molecular weight of the peptide may vary, e.g., from about 26,000 to about 70,000 daltons.

The peptides of the present invention may be formed by a variety of methods. One method of forming a peptide of the present invention is by inserting a nucleic acid molecule encoding a fungal pheromone into a selected position of a nucleic acid molecule encoding a colicin, or a channel forming domain thereof, then transfecting the mutant plasmid into a host cell, e.g., *E. coli*, to produce the peptide. In an alternative embodiment, portions of the peptide may be made separately, e.g., synthetically, or by recombinant means, and later linked by known methods.

In one embodiment, the peptides of the present invention are useful in treating infections of *Candidas* or *Aspergillus* or *Magnaporthes* or *Fusarium*. Exemplary infections are those created by *Candida albicans, Candida tropicalis, Candida parapsilokis, Candida krusei, Candida dubliniensis, Cryptococcus neoformans, A. fumigatus, A. flavus, A. niger, Magnaporthe grisea* and *Fusarium moniforme*.

The invention further provides nucleic acid molecules that encode the peptides of the invention. The invention also provides vectors comprising the nucleic acid molecules, e.g., expression vectors. The invention also provides cells, e.g., host cells, comprising the vectors of the invention.

Host cells, including bacterial cells such as *E. coli*, insect cells, yeast or mammalian cells (such as Chinese hamster ovary cells (CHO) or COS cells), can be used to produce the peptides of the invention. Other suitable host cells are known to those skilled in the art. The invention thus provides methods for producing the peptides of the invention comprising the steps of culturing the host cells of the invention and isolating the peptides of the invention therefrom.

In another embodiment, the invention provides a method for preparing a peptide which inhibits growth of a fungus comprising: (i) inserting a nucleic acid molecule encoding colicin, or a channel forming domain thereof, into a selected position of a nucleic acid molecule encoding a fungal targeting agent, e.g., a pheromone; (ii) transfecting the mutant plasmid into a host cell, e.g., an *E. coli* cell; and (iii) allowing said host cell to produce said peptide. In further embodiments, the peptide may be purified from the cells.

In another embodiment, the invention provides a method for preparing a fusion peptide comprising: (i) incorporating a nucleic acid molecule encoding the peptide chain of colicin Ia with a nucleic acid molecule encoding a fungal pheromone such as *Candida albicans* α-mating pheromone; (ii) introducing said nucleic acid molecule encoding the peptide chain of colicin Ia incorporated with said fungal pheromone a following the C-terminus of the colicin Ia to form a nucleic acid molecule that encodes a 639 residue peptide.

In another embodiment, the invention provides a method for preparing a fusion peptide comprising: (i) incorporating a nucleic acid molecule encoding a peptide chain of colicin Ia with a nucleic acid molecule encoding a fungal pheromone such as *Candida albicans* α-mating pheromone; (ii) introducing said nucleic acid molecule before the N-terminus of said colicin Ia to form a nucleic acid molecule that encodes a 639 residue peptide.

In one embodiment, the invention provides a method of treating a subject having a fungal infection comprising: administering to a subject a therapeutically effective amount of a fusion peptide of the present invention, e.g., a peptide comprising a colicin Ia with a fungal targeting agent, e.g., a pheromone. Said subject may have a *Candidas* or *Aspergillus* or *Magnaporthe* or *Fusarium* infection. Specifically, *Candidas* or *Aspergillus* or *Magnaporthe* or *Fusarium* may be selected from the group consisting of *Candida albicans, Candida tropicalis, Candida parapsilokis, Candida krusei, Candida dubliniensis, Cryptococcus neoformans, A. fumigatus, A. flavus, A. niger, Magnaporthe grisea* and *Fusarium moniforme*. The peptides of the instant invention can also be used to treat clinical fugal infections and other fungal infections in crops.

The peptides of the invention can be incorporated into pharmaceutical compositions suitable for administration to a subject. In a preferred embodiment, the pharmaceutical composition comprises a peptide of the invention comprising the *C. albicans* α-pheromone and a pharmaceutically acceptable carrier.

The term, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous or parenteral administration (e.g., by injection). Depending on the route of administration, the active compound may be coated in a material to protect the compound from the action of acids and other natural conditions, which may inactivate the compound.

DETAILED DESCRIPTION

Figure 1:
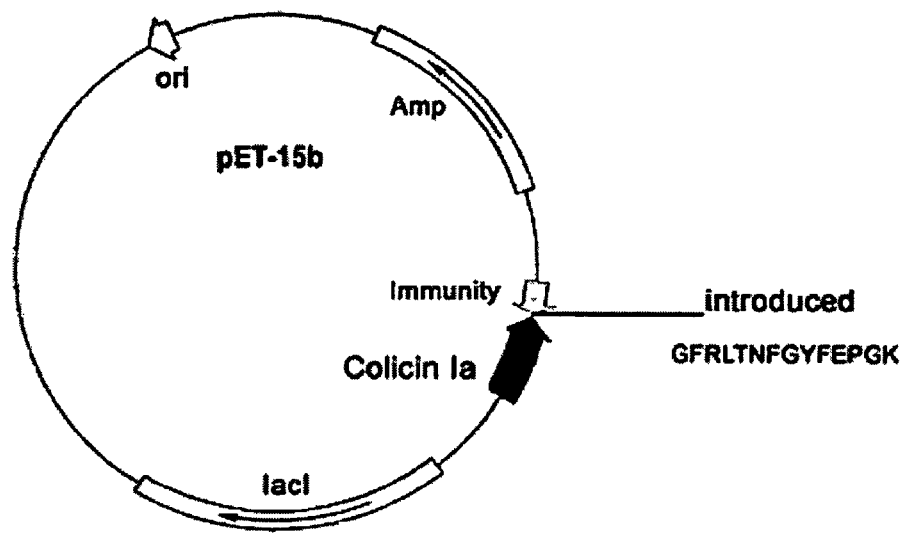
FIG. 1 schematically depicts the structure of a recombinant plasmid that contains the gene of colicin Ia with the gene of *Candida albicans* α-mating pheromone inserted following the C-terminus of colicin Ia in the plasmid pET-15b to form a plasmid referred to herein as pCHCCA1.
Figure 2:
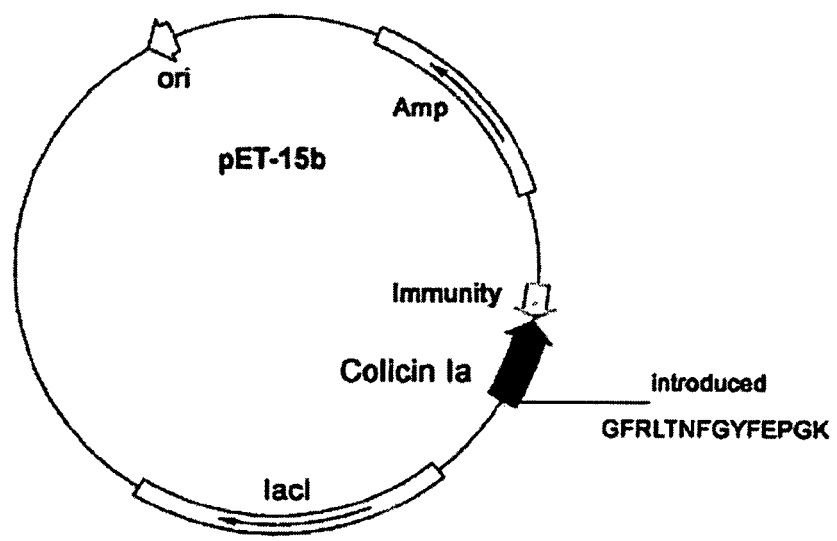
FIG. 2 schematically depicts the structure of a recombinant plasmid that contains the gene of colicin Ia with the gene of *Candida albicans* α-mating pheromone inserted following the N-terminus of colicin Ia in the plasmid pET-15b to form the plasmid referred to herein as pCHCCA2.

The antifungal peptides of the present invention comprise a fungi specific targeting agent e.g., a fungal pheromone, and one or more channel-forming colicins or channel-forming domains thereof. The molecular structure is generally either the C-terminus of a colicin or channel-forming domain thereof, linked with the N-terminus of the fungal specific targeting agent, or the N-terminus of the colicin or channel forming domain thereof, linked with the C-terminus of a fungal specific targeting agent. Although full-length colicin may be used in the methods and compositions of the invention, in some embodiments, only a channel-forming domain is used. In a preferred embodiment, the colicin channel-forming domain consists essentially of amino acids 451-626 of colicin Ia.

Colicins are protein toxins produced by strains of *E. coli*. They are generally classified into groups corresponding to the outer membrane receptor on sensitive *E. coli* cells to which they bind, with colicins that bind to the BtuB protein, the high affinity receptor for vitamin B12, being known as the E group. E-type colicins are about 60 kDa proteins that have three functional domains each implicated in one of the three stages of cell killing. The C-terminal domain carries the cytotoxic activity, the central domain carries the receptor-binding activity, and the N-terminal domain mediates translocation of the cytotoxic domain across the outer membrane. Three cytotoxic activities are found amongst E-type colicins: (i) a pore-forming ion channel that depolarizes the inner membrane (colicin E1); (ii) an H—N—H endonuclease activity that degrades chromosomal DNA (colicins E2, E7, E8 and E9);

and (iii) ribonuclease activities (colicin E3, E4, E5 and E6). Colicin-producing bacteria are resistant against the action of their own colicin through possession of a small immunity protein that inactivates the cytotoxic domain. After binding to *E. coli* cell surface receptors, E-type colicins are translocated to their site of action by a tol dependent translocation system.

The peptides of the present invention maybe prepared by inserting a nucleic acid molecule encoding a fungal pheromone into the selected position of a nucleic acid molecule encoding a colicin, or a channel forming fragment thereof. The resulting transfected mutant plasmid may then inserted into a host cell, e.g., *E. coli*, to produce the peptide. Colicin Ia has the nucleic acid sequence set forth in SEQ ID NO: 1. *Candida albicans* α-mating pheromone has the nucleic acid sequence set forth in SEQ ID NO:2 and the amino acid sequence set forth in SEQ ID NO:3.

The peptides of the invention may be used to treat subjects having a fungal infection, e.g., *Candidas, Cryptococcus, Aspergillus, Magnaporthes* or *Fusariums*. Exemplary fungal infections are oral thrush, oesophageal thrush (Oesophagitis), cutaneous (skin) candidiasis, vaginal yeast infection or candida vaginitis, balanitis, and systemic candidiasis. The peptides of the invention may also be used to treat devastating fungal infections in crops.

EXAMPLES

Example 1

A fusion peptide that has been identified as pheromonicin-CA1(Ph-CA1) was created incorporating a peptide chain of colicin Ia with a *Candida albicans* α-mating pheromone, wherein the pheromone was c-terminal to the colicin Ia to produce a polynucleotide having the nucleic acid sequence of SEQ ID NO:4 which encodes a polypeptide having the amino acid sequence of SEQ ID NO:5.

Example 2

A second fusion peptide denominated as pheromonicin-CA2 (Ph-CA2) was created by incorporating a peptide chain of colicin Ia with a *Candida albicans* α-mating pheromone, wherein the pheromone is n-terminal to the colicin Ia, to produce a polynucleotide having nucleic acid sequence of SEQ ID NO:6 which encodes a polypeptide having the amino acid sequence of SEQ ID NO:7.

Results

Ph-CA1 had definite antifungal effect on *Candida albicans* (ATCC 10231) in vitro and in vivo. In contrast, Ph-CA2 almost had no effect. One in vitro cell growth inhibition assay was performed with M-H or PDA solid mediums. About 5 µl Cells ($10^8$ CFU/ml) of *Candida albicans* (ATCC 10231), *Cryptococcus neoformans* (Huaxi 30168 strain, clinical isolated strain by West China Hospital, Sichuan University), *Aspergillus flavus* (Huaxi 30255 strain), *Magnaporthe grisea* (ACCC 30320 strain, Species Conservation Center, Chinese Academy of Agriculture Sciences), or *Fusarium moniforme* (ACCC 30133 strain) were inoculated on the surface of 10 ml M-H or PDA solid mediums contained in disks. Then 50-100 µl amphotericin B (0.5 µg to 2 µg/ml) or fluconazole (3 µg/ml) or tricyclazole (0.05 mg to 5 mg/ml) or Ph-CA1 (25 to 50 µg/ml) either rinsed in a piece of filter paper or contained in a container then being placed on the surface of the medium, and incubated at 35° C. for 2 to 4 days.

Figure 3:
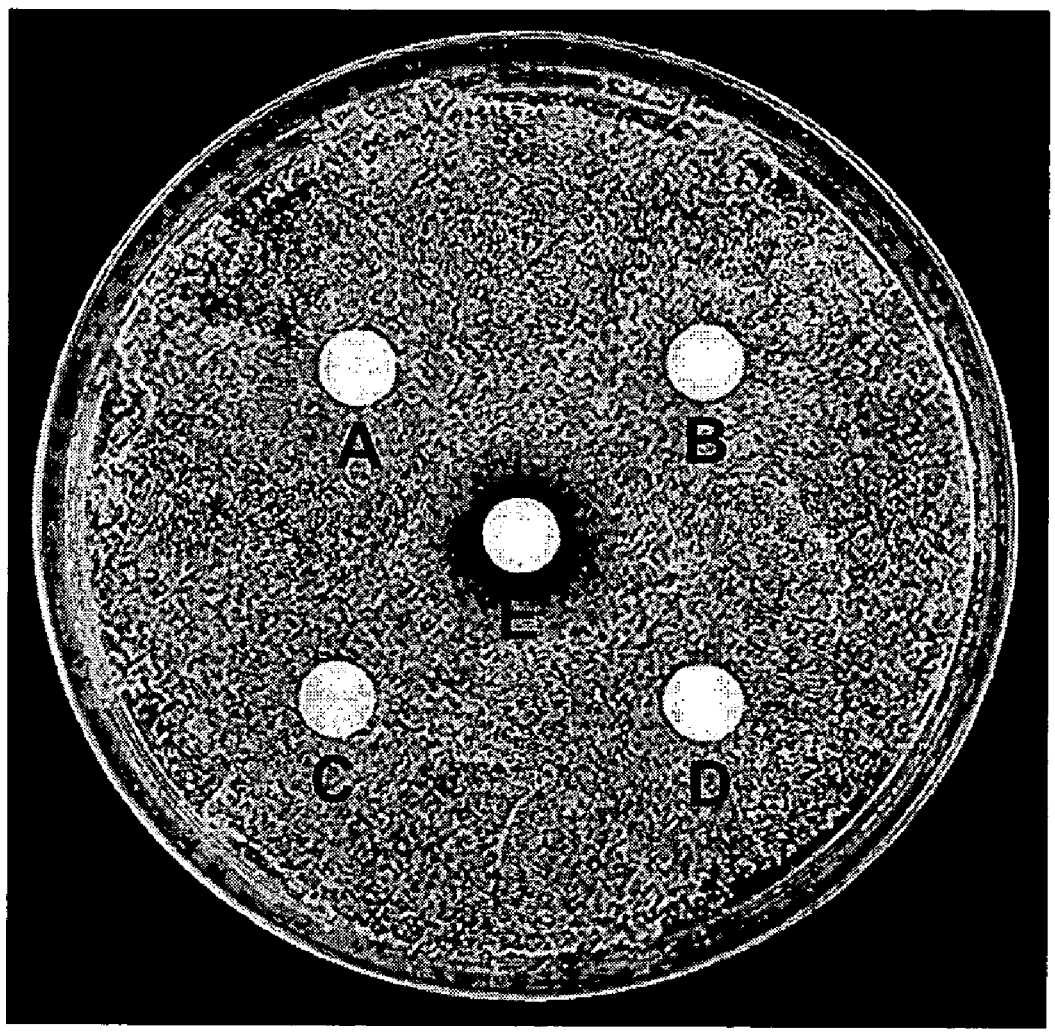
FIG. 3 depicts a growth inhibition assay wherein ATCC 10231 *C. albicans* cells were grown in M-H solid medium and exposed to (A) borate stock solution as control, (B) 50 μl amphotericin B (1 μg/ml), (C) 50 μl fluconazole (3 μg/ml), (D) 50 μl pheromonicin-SA (Ph-SA)(50 μg/ml), the fusion peptide against *Staphylococcus aureus* and (E) 50 μl pheromonicin-CA1 (Ph-CA1)(50 μg/ml), the peptide produced by the pCHCCA1 plasmid.

As shown in FIG. 3, only an inhibition-zone surrounds Ph-CA1, while no similar zones were observed with other agents. FIGS. 7 to 10 show that Ph-CA1 had definite antifungal effects against corresponding *Cryptococcus neoformans, Aspergillus flavus, Magnaporthe grisea* and *Fusarium moniforme* cells. On a molar basis, such antifungal effects were one hundred to one thousand times greater than that of known antifungal antibiotics.

In vitro cell growth inhibition assays were performed in 100 ml Klett flasks containing 10 ml of M-H medium which were monitored turbimetrically with a BioRad 550 microplate reader at OD595 nm every 60 min. The filament (mycelium) precipitation at the bottom of flask was counted with a digital photo-recorder every 6 hrs. Cells were inoculated to an initial cell density of about $2.5 \times 10^5$ CFU/ml and shaken at 200 rpm on an orbital shaker at 35° C. Sedimentary fungal filaments appeared in about 36 hrs growing.

Ph-CA1 and Ph-CA2 were added at the start of the culture. The same amount of borate stock solution (50 mM borate, PH9.0), Ph-SA (pheromonicin constructed by colicin Ia and staphylococcal pheromone AgrD1)(10 µg/ml) and several antibiotics preparations (2 µg/ml amphotericin B, 6 µg/ml fluconazole) were used as controls. All assays were expressed in turbidometric absorbance units measured at 595 nm and pictures of the filament sedimentation at the bottom of the flask were taken.

Figure 4:
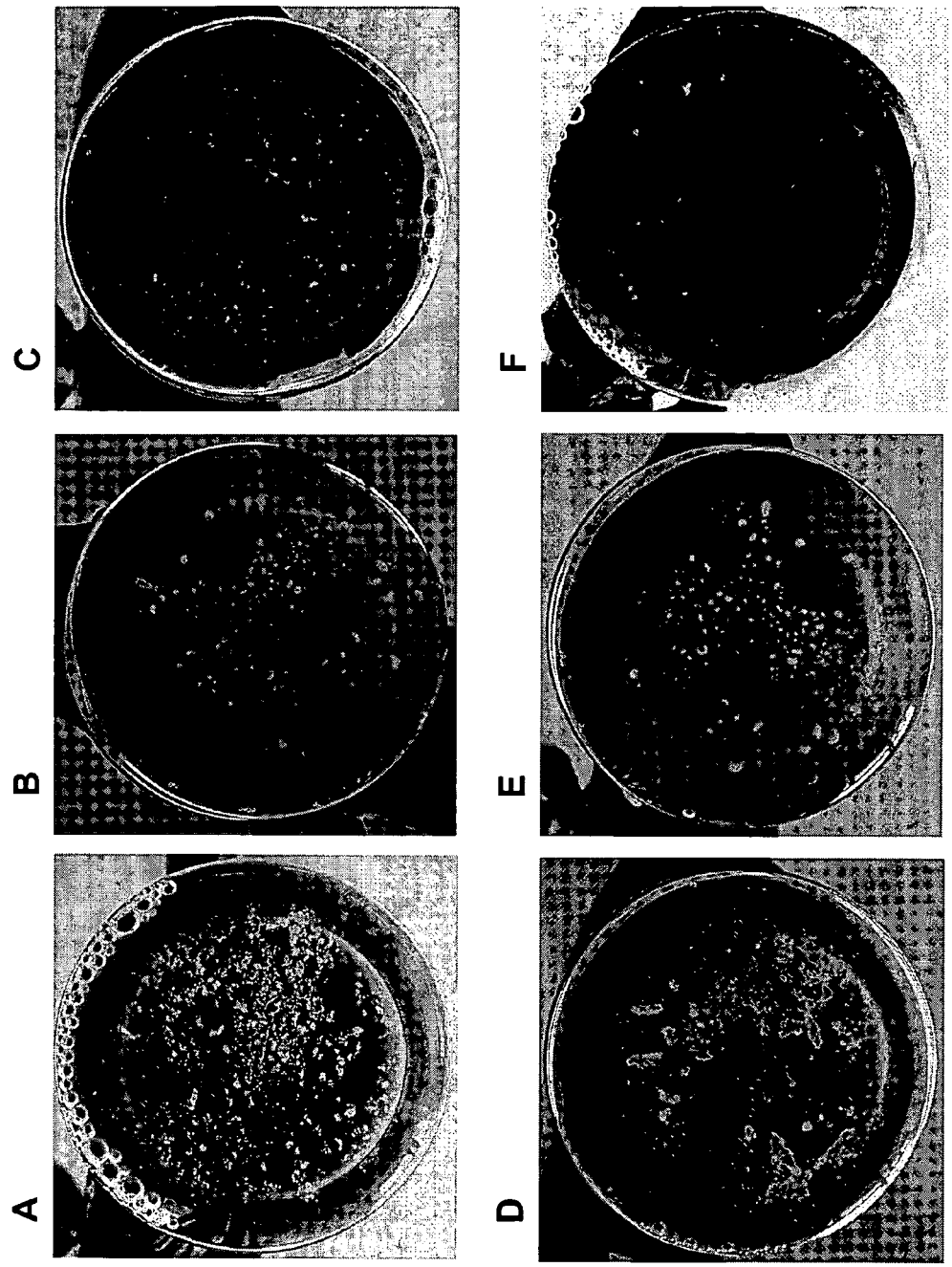
FIG. 4 depicts the inhibition effects of Ph-CA against the growth of ATCC 10231 *C. albicans* cells in M-H liquid medium. The amount of sedimentary fungal filaments at the bottom of flasks indicated the inhibition effects of treatment agents. (A) Control, (B) fluconazole, (C) amphotericin B, (D) Ph-SA, (E) Ph-CA2 produced by pCHCCA2 plasmid and (F) Ph-CA1.
Figure 5:
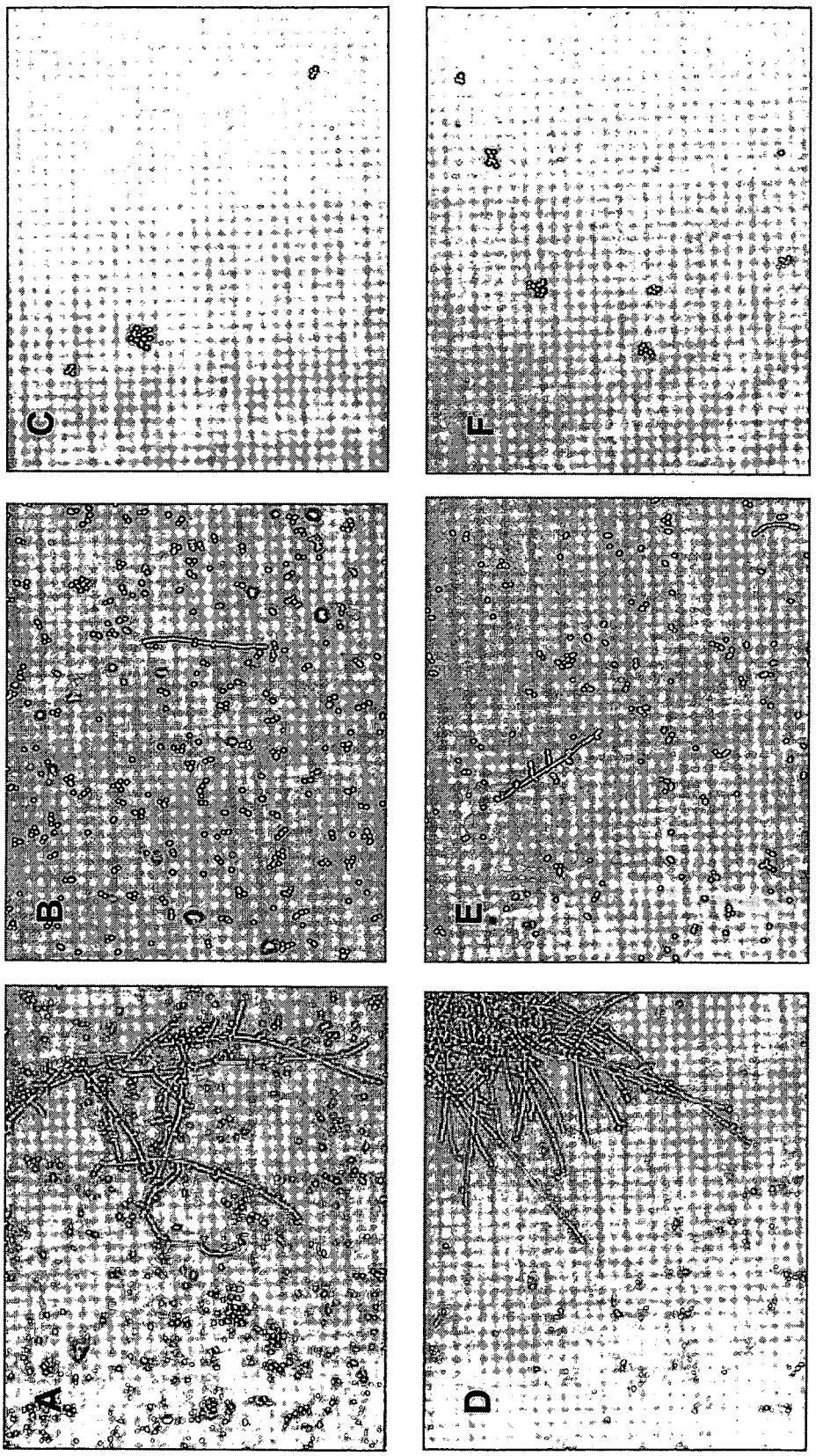
FIG. 5 depicts the inhibition effects of Ph-CA against the growth of *C. albicans* cells in liquid medium. The amount of spores and filaments of ATCC 10231 *C. albicans* cells indicated the inhibition effects. (A) Control, (B) fluconazole, (C) amphotericin B, (D) Ph-SA, (E) Ph-CA2 (F) Ph-CA1. X400.

Fluconazole and Ph-SA had no effect on the growth of *C. albicans* compared to untreated controls. In contrast, 10 µg/ml Ph-CA1 completely inhibited *C. albicans* growth, as did 2 µg/ml amphotericin B. 10 µg/ml Ph-CA2 had about 30% of the inhibition effect as the Ph-CA1. Considering the difference in molecular weight between Ph-CA1 (70 kDa) and amphotericin B (about 0.9 kDa), the inhibitory effect of Ph-CA1 against *C. albicans* was approximately ten times greater, on a molar basis, than that of amphotericin B (see FIG. 4). The spores and filaments of 2 µl treated medium were dripped on a slide and observed under microscope. In comparison with control and other treatments, spores were scarcely observed in the amphotericin B and Ph-CA1 (see FIG. 5).

Figure 6:
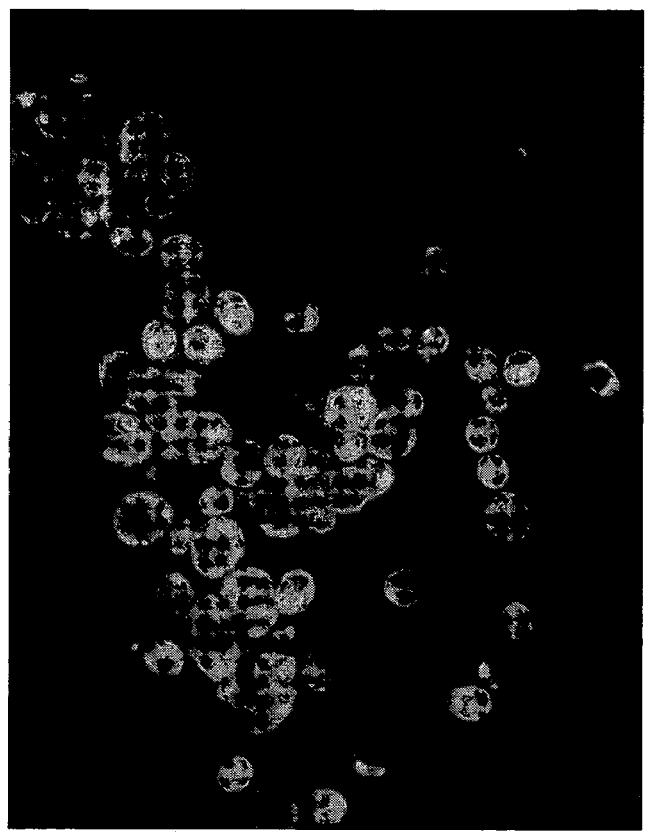
FIG. 6 depicts the fluorescent imaging of ATCC 10231 *C. albicans* cells treated by Ph-CA1 and stained with 50 nM FITC/600 nM propidium iodide. (A) Control, cells were stained by FITC as green, (B) cells became red after 24 hrs Ph-CA1 treatment (10 μg/ml). X400.
Figure 6:
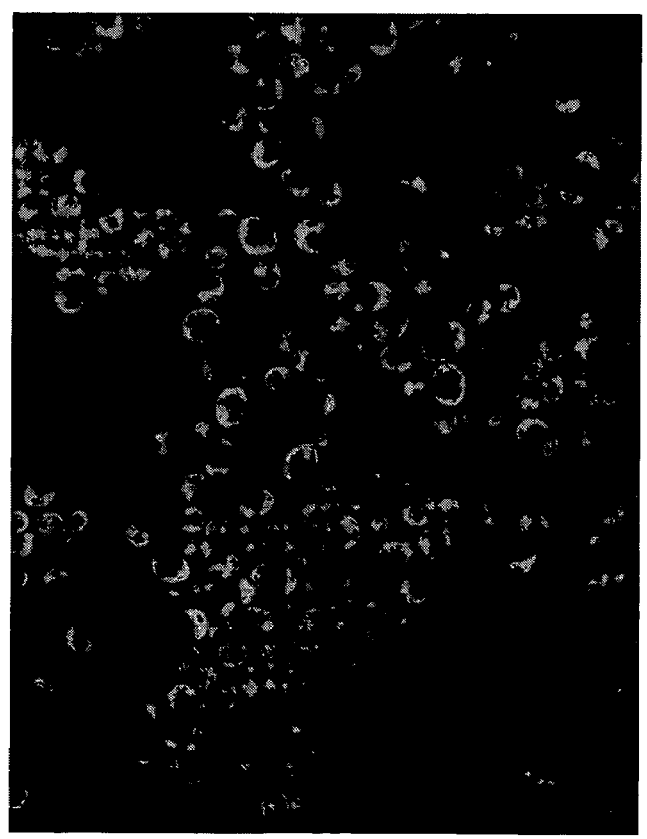
Figure 7:
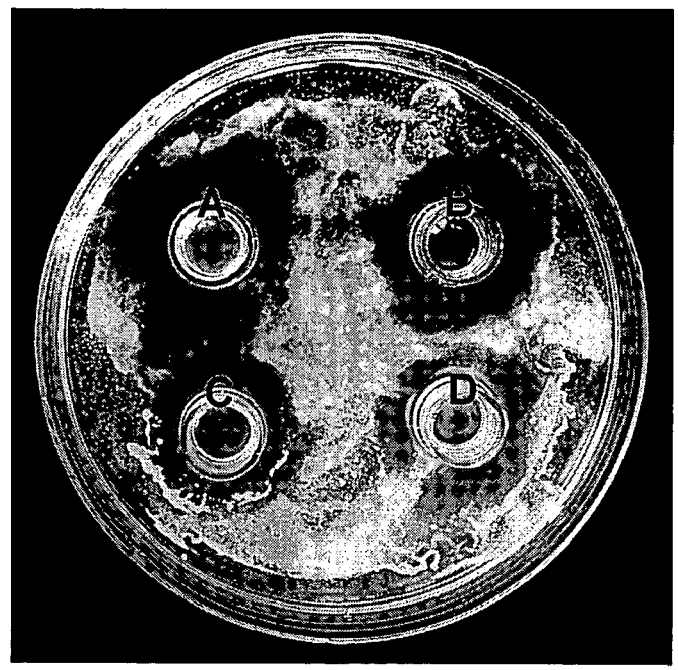
FIG. 7 depicts a growth inhibition assay wherein Huaxi 30168 *Cryptococcus neoformans* cells were grown in M-H solid medium and exposed to (A) and (B) 100 μl amphotericin B (2 μg and 0.5 μg/ml respectively), (C) and (D) 100 μl Ph-CA1 (50 μg and 25 μg/ml respectively).
Figure 8:
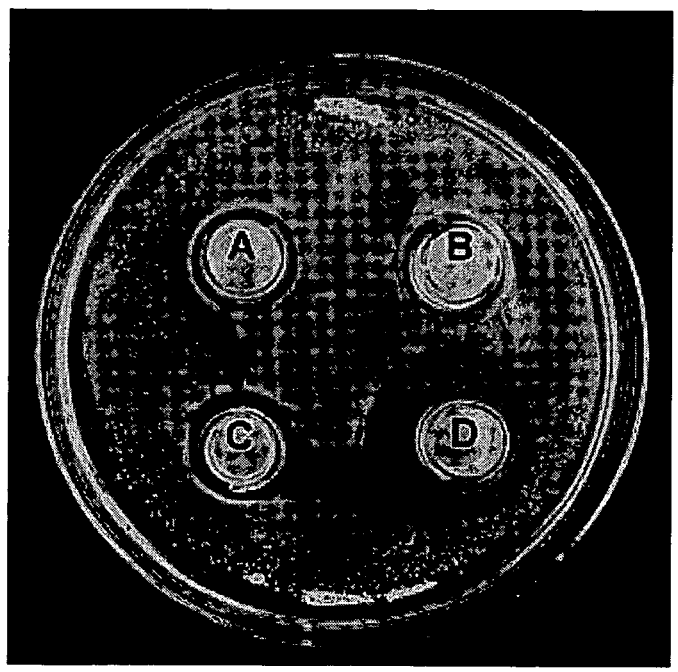
FIG. 8 depicts a growth inhibition assay wherein Huaxi 30255 *Aspergillus flavus* cells were grown in PDA solid medium and exposed to (A), (B) and (C) 100 μl tricyclazole (5 mg, 0.5 mg, and 0.05 mg/ml respectively), (D) 100 μl Ph-CA1 (50 μg/ml).
Figure 9:
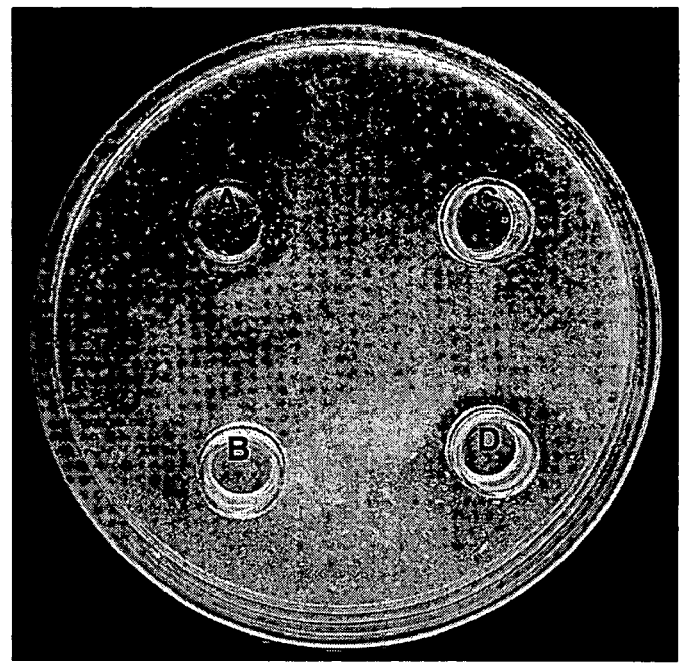
FIG. 9 depicts a growth inhibition assay wherein ACCC 30320 *Magnaporthe grisea* cells were grown in PDA solid medium and exposed to (A) 100 μl amphotericin B (0.5 μg/ml), (B) 100 μl tricyclazole (0.5 mg/ml), (C) and (D) 100 μl Ph-CA1 (25 μg and 50 μg/ml respectively).
Figure 10:
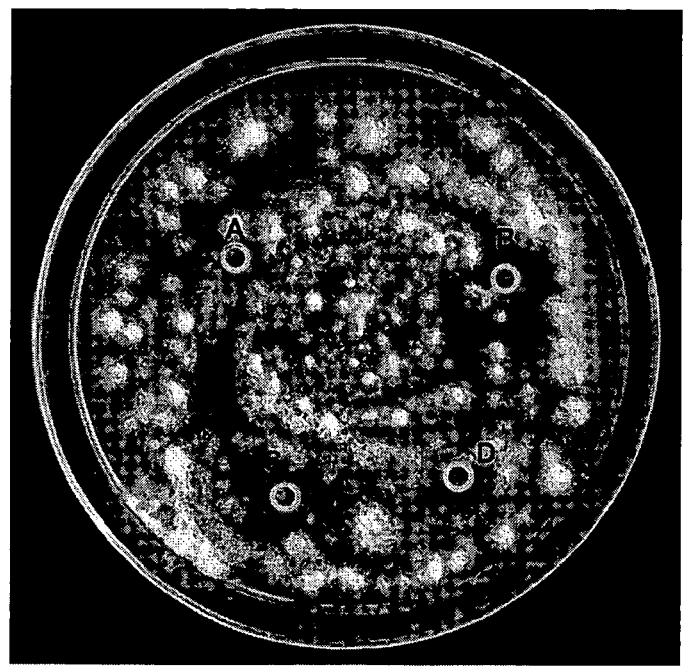
FIG. 10 depicts a growth inhibition assay wherein ACCC 30133 *Fusarium moniforme* cells were grown in PDA solid medium and exposed to (A) control, (B) 100 μl amphotericin B (0.5 μg/ml), (C) Ph-CA1 100 μl Ph-CA1 (50 μg/ml) and (D) 100 μl tricyclazole (0.5 mg/ml).

FIG. 6 shows that after 24 hrs of incubation with Ph-CA1 (10 µg/ml), cell membrane of most *C. albicans* cells (stained by FITC as green in the presence of propidium iodide) was damaged thus the propidium iodide entered into the cell to stain cells red.

Figure 11:
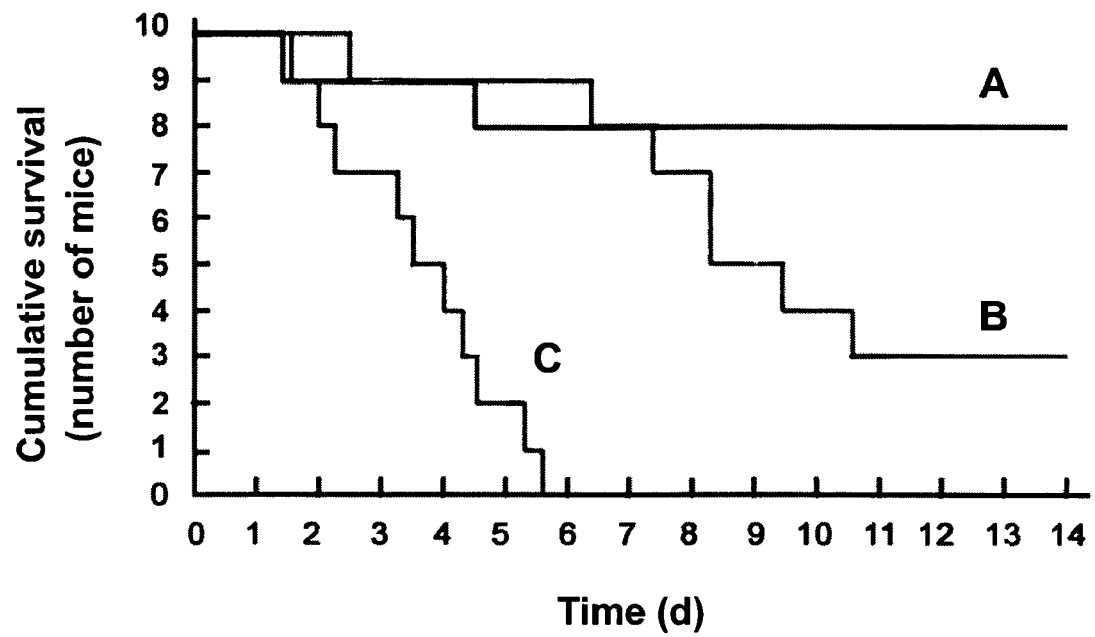
FIG. 11 depicts in vivo activity of Ph-CA1 against systemic candidiasis. The *C. albicans* infected mice were untreated or treated by intraperitoneal amphotericin B or Ph-CA1.

KungMing mice, half male and half female, weighing 18-22 g were injected intraperitoneally with 0.5 ml of *C. albicans* (ATCC 10231), $10^8$ CFU/ml. One hour after *C. albicans* injection, mice were injected intraperitoneally with 0.9% saline (A) alone as control (n=10) (C), or with amphotericin B (n=10, 1 µg/gm/day) (B), or with Ph-CA1 (n=10, 5 µg/gm/day) (A) daily for 14 days. The number of surviving animals was determined every 24 hours (FIG. 11).

Figure 12:
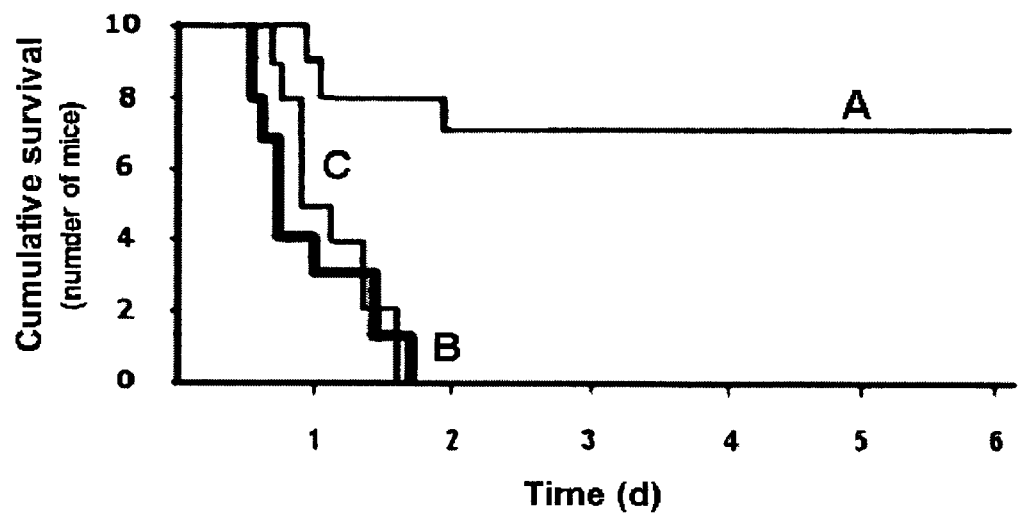
FIG. 12 depicts in vivo activity of Ph-CA1 against systemic candidiasis. The *C. albicans* infected mice were untreated or treated by intravenous amphotericin B or Ph-CA1.

KungMing mice, half male and half female, weighing 18-22 g were injected intraperitoneally with 0.7 ml of *C. albicans* (ATCC 10231), $10^8$ CFU/ml. One hour after *C. albicans* injection, mice were injected in the tail vein with 0.9% saline alone as control (n=10) (C), or with amphotericin B (n=10, 1 µg/gm) (B), or with Ph-CA1 (n=10, 5 µg/gm) (A). The mice were then injected intraperitoneally with 0.9% saline alone, or with amphotericin B (n=10, 1 µg/gm), or with Ph-CA1 (n=10, 5 µg/gm) each day. The number of surviving animals was determined every 24 hours (FIG. 12). Considering the difference in molecular weight between Ph-CA1 (70 kDa) and amphotericin B (about 0.9 kDa), the in vivo antifungal activity of Ph-CA1 against systemic candidiasis was at least twenty times greater, on a molar basis, than that of amphotericin B.

Figure 13:
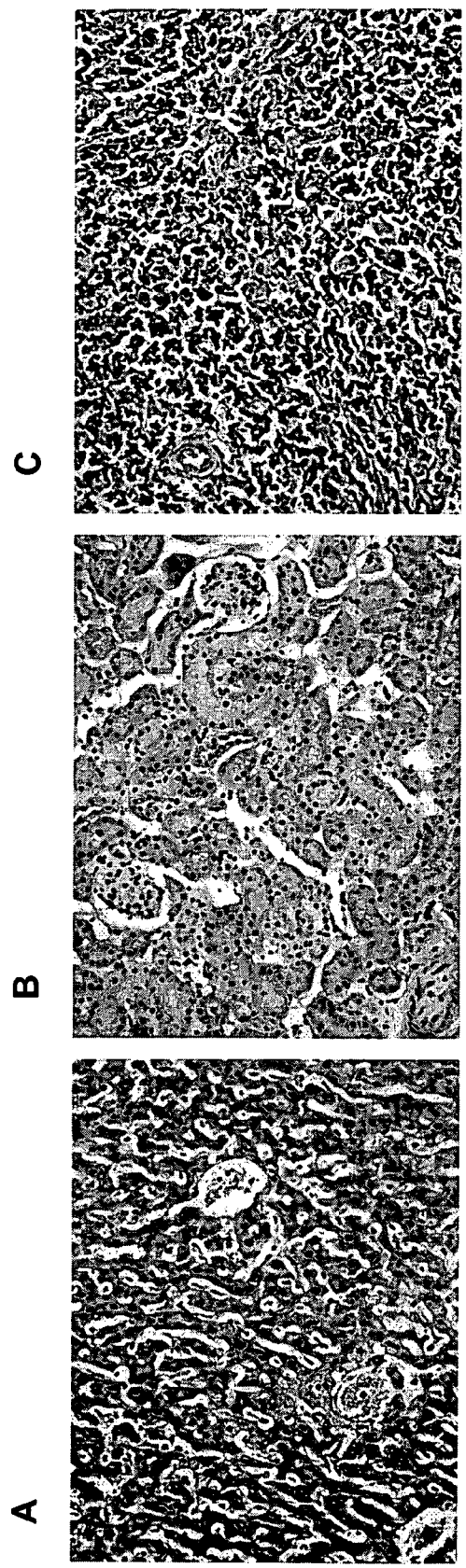
FIG. 13 depicts the microscopic view of visceral organs of mice treated with Ph-CA1 30 days. (A) liver, (B) kidney and (C) spleen stained with hematoxylin and eosin. 100×.

KungMing mice (n=10), half male and half female, weighing 18-22 g were injected intraperitoneally with Ph-CA1 (200 µg/mouse/day) for 20 days. The bodyweight of all mice was increased. There was no microscopic evidence of necrosis or inflammation in the livers, kidneys or spleens of mice (FIG. 13).

A 300 m² rice field (seed, gangyou 725) with *Magnaporthe grisea* infection was randomly divided as three zones. The middle 100 m² area was treated with water spraying twice as control, the left 100 m² area was treated with tricyclazole spraying twice (0.5 mg/ml and 1 mg/ml) and the right 100 m² area was treated with Ph-CA1 spraying twice (1 µg/ml and 2 µg/ml) at the tillering stage. The time interval between two sprayings was 7 days. Each 200 leaves were randomly examined in control and treatment areas to determine the protecting efficacy of Ph-CA1. The data are depicted below in Table I.

TABLE I

| Examining date | Grades of impaired leaves | | | | | | Incident rate | Infected index | Protecting efficacy |
|---|---|---|---|---|---|---|---|---|---|
| | 0 | 1 | 3 | 5 | 7 | 9 | | | |
| One day Before Treatment | 152 | 27 | 14 | 6 | 1 | | 24 | 5.88 | |
| After Treatment | 89 | 57 | 30 | 7 | 7 | 8 | 55.5 | 17.38 | |
| Seven days Tricyclazole | 172 | 10 | 12 | 6 | | | 14 | 4.22 | 75.83 |
| Ph-CA1 | 67 | 12 | 13 | 8 | | | 16.5 | 5.05 | 70.94 |

Another 300 m² rice field (seed, gangyou 725) with *Magnaporthe grisea* infection was randomly divided as three zones. The middle 100 m² area was treated with water spraying once as control, the left 100 m² area was treated tricyclazole spraying once (1 mg/ml) and the right 100 m² area was treated with Ph-CA1 spraying once (2 μg/ml) at the head stage. About 200 ears were randomly examined in control and treatment areas to determine the protecting efficacy of Ph-CA1. The data are depicted below in Table II.

TABLE II

| | Grades of impaired ears | | | | | | Impaired ears rate | Infected index | Damage rate |
|---|---|---|---|---|---|---|---|---|---|
| | 0 | 1 | 3 | 5 | 7 | 9 | | | |
| Control | 178 | 33 | 22 | 11 | 2 | 2 | 28.6% | 8.33 | 4.2% |
| Tricyclazole | 184 | 16 | 9 | 2 | 2 | 0 | 13.62% | 3.5 | 1.63% |
| Ph-CA1 | 218 | 19 | 5 | 0 | 0 | 0 | 9.92% | 1.56 | 0.53% |

In both of the above in vivo protecting assays, the concentration of Ph-CA1 used was approximately 500 times smaller than that of tricyclazole. On a molar basis, the protecting effects of Ph-CA1 were three hundred times greater than that of tricyclazole. With these two factors taken together, the total effects of Ph-CA1 against rice blast disease was approximately $10^4$ to $10^5$ times greater than that of tricyclazole.

---

What is claimed is:

1. An isolated peptide comprising a *Candidas albicans* alpha-mating pheromone and a channel forming domain, wherein said peptide consists essentially of the amino acid sequence of SEQ ID NO: 5.

2. A pharmaceutical composition comprising the peptide of claim 1 and a pharmaceutically acceptable carrier.

3. The peptide of claim 1, wherein said *Candida albicans* alpha-mating pheromone consists of SEQ ID NO: 3.

4. The pharmaceutical composition of claim 2, wherein said peptide comprises the amino acid sequence set forth in SEQ ID NO: 5.

* * * * *